(12) United States Patent
Melvin

(10) Patent No.: US 7,361,191 B2
(45) Date of Patent: Apr. 22, 2008

(54) HEART WALL ACTUATION DEVICE FOR THE NATURAL HEART

(75) Inventor: David Boyd Melvin, Loveland, OH (US)

(73) Assignee: The University of Cincinnati, Cincinnati, OH (US)

( * ) Notice: Subject to any disclaimer, the term of this patent is extended or adjusted under 35 U.S.C. 154(b) by 426 days.

(21) Appl. No.: 10/618,986

(22) Filed: Jul. 14, 2003

(65) Prior Publication Data

US 2004/0024286 A1 Feb. 5, 2004

Related U.S. Application Data

(63) Continuation of application No. 09/850,554, filed on May 7, 2001, now Pat. No. 6,592,619, which is a continuation-in-part of application No. 09/326,416, filed on Jun. 4, 1999, now Pat. No. 6,520,904, which is a continuation-in-part of application No. 09/316,611, filed on May 21, 1999, now abandoned, which is a continuation-in-part of application No. 09/165,887, filed on Sep. 30, 1998, now Pat. No. 6,221,103, which is a continuation-in-part of application No. 08/581,914, filed on Jan. 2, 1996, now Pat. No. 5,957,977.

(51) Int. Cl.
*A61M 1/10* (2006.01)
(52) U.S. Cl. .................... 623/3.11; 600/16
(58) Field of Classification Search ............... None
See application file for complete search history.

(56) References Cited

U.S. PATENT DOCUMENTS 2,826,193 A 3/1958 Vineberg (Continued)

FOREIGN PATENT DOCUMENTS

EP 119357 9/1984

(Continued)

OTHER PUBLICATIONS

Melvin, D.V.; Conkle, D.; Roberts, A; Stinson, E.;, "*Cardiac Performance and Myocardial Contractility After Experimental Mechanical Ventricular Assistance*", J. Thoracic and Cardiovascular Surgery vol. 65, No. 6, Jun. 1973.

(Continued)

*Primary Examiner*—Brian E. Pellegrino
(74) *Attorney, Agent, or Firm*—Wood, Herron & Evans, LLP

(57) ABSTRACT

An actuation system for assisting the operation of the natural heart comprises a framework for interfacing with a natural heart, through the wall of the heart, which includes an internal framework element configured to be positioned within the interior volume of a heart and an external framework element configured to be positioned proximate an exterior surface of the heart. The internal framework is flexibly suspended with respect to the external frame. An actuator system is coupled to the framework and configured to engage an exterior surface of the heart. The actuator system comprises an actuator band extending along a portion of a heart wall exterior surface. The actuator band is selectively movable between an actuated state and a relaxed state and is operable, when in the actuated state, to assume a predetermined shape and thereby indent a portion of the heart wall to effect a reduction in the volume of the heart. A drive apparatus is coupled to the actuator band and is operable for selectively moving the actuator band between the relaxed and actuated states to achieve the desired assistance of the natural heart.

18 Claims, 9 Drawing Sheets

U.S. PATENT DOCUMENTS

| | | |
|---|---|---|
| 3,053,249 A | 9/1962 | Smith |
| 3,455,298 A | 7/1969 | Anstadt |
| 3,513,836 A | 5/1970 | Sausse |
| 3,590,815 A | 7/1971 | Schiff |
| 3,613,672 A | 10/1971 | Schiff |
| 3,668,708 A | 6/1972 | Tindal |
| 3,713,439 A | 1/1973 | Cabezudo |
| 3,791,388 A | 2/1974 | Hunter et al. |
| 3,827,426 A | 8/1974 | Page et al. |
| 3,983,863 A | 10/1976 | Janke et al. |
| 4,192,293 A | 3/1980 | Asrican |
| 4,536,893 A | 8/1985 | Parravicini |
| 4,621,617 A | 11/1986 | Sharma |
| 4,690,134 A | 9/1987 | Snyders |
| 4,809,676 A | 3/1989 | Freeman |
| 4,846,831 A | 7/1989 | Skillin |
| 4,904,255 A | 2/1990 | Chareire et al. |
| 4,936,857 A | 6/1990 | Kulik |
| 4,957,477 A | 9/1990 | Lundback |
| 5,109,843 A | 5/1992 | Melvin et al. |
| 5,119,804 A | 6/1992 | Anstadt |
| 5,131,905 A | 7/1992 | Grooters |
| 5,139,517 A | 8/1992 | Corral |
| 5,169,381 A | 12/1992 | Snyders |
| 5,192,314 A | 3/1993 | Daskalakis |
| 5,201,880 A | 4/1993 | Wright et al. |
| 5,256,132 A | 10/1993 | Snyders |
| 5,258,021 A | 11/1993 | Duran |
| 5,334,217 A | 8/1994 | Das |
| 5,345,949 A | 9/1994 | Shlain |
| 5,358,519 A | 10/1994 | Grandjean |
| 5,370,685 A | 12/1994 | Stevens |
| 5,383,840 A | 1/1995 | Heilman et al. |
| 5,385,528 A | 1/1995 | Wilk |
| 5,484,391 A | 1/1996 | Buckman, Jr. et al. |
| 5,487,760 A | 1/1996 | Villafana |
| 5,533,958 A | 7/1996 | Wilk |
| 5,571,176 A | 11/1996 | Taheri |
| 5,581,176 A | 12/1996 | Lee |
| 5,593,424 A | 1/1997 | Northrup, III |
| 5,655,548 A | 8/1997 | Nelson et al. |
| 5,702,343 A | 12/1997 | Alferness |
| 5,709,695 A | 1/1998 | Northrup, III |
| 5,713,954 A | 2/1998 | Rosenberg et al. |
| 5,738,626 A | 4/1998 | Jarvik |
| 5,738,627 A | 4/1998 | Kovacs et al. |
| 5,749,883 A | 5/1998 | Halpern |
| 5,800,528 A | 9/1998 | Lederman et al. |
| 5,824,071 A | 10/1998 | Nelson et al. |
| 5,910,124 A | 6/1999 | Rubin |
| 5,957,977 A | 9/1999 | Melvin |
| 5,961,440 A | 10/1999 | Schweich, Jr. et al. |
| 6,019,722 A | 2/2000 | Spence et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,077,214 A | 6/2000 | Mortier et al. |
| 6,085,754 A | 7/2000 | Alferness et al. |
| 6,099,460 A * | 8/2000 | Denker ........................ 600/16 |
| 6,110,100 A | 8/2000 | Talpade |
| 6,123,662 A | 9/2000 | Alferness et al. |
| 6,125,852 A | 10/2000 | Stevens et al. |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,179,791 B1 | 1/2001 | Krueger |
| 6,183,411 B1 | 2/2001 | Mortier et al. |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,293,906 B1 | 9/2001 | Vanden Hoek et al. |
| 6,319,231 B1 | 11/2001 | Andrulitis |
| 6,324,430 B1 | 11/2001 | Zarinetchi et al. |
| 6,324,431 B1 | 11/2001 | Zarinetchi et al. |
| 6,332,863 B1 | 12/2001 | Schweich, Jr. et al. |
| 6,332,864 B1 | 12/2001 | Schweich, Jr. et al. |
| 6,332,893 B1 | 12/2001 | Mortier et al. |
| 6,375,611 B1 | 4/2002 | Voss et al. .................. 600/210 |
| 2001/0016675 A1 | 8/2001 | Mortier et al. |
| 2001/0047122 A1 | 11/2001 | Hoek et al. |
| 2003/0023132 A1 | 1/2003 | Melvin et al. |
| 2003/0130731 A1* | 7/2003 | Vidlund et al. ............ 623/2.37 |

FOREIGN PATENT DOCUMENTS

| | | |
|---|---|---|
| EP | 0583012 | 2/1988 |
| SU | 1191-076 A | 11/1985 |
| WO | WO 98/29041 | 7/1998 |
| WO | WO 99/30647 | 6/1999 |
| WO | WO 99/53977 | 10/1999 |
| WO | WO 00/02500 | 1/2000 |
| WO | WO 00/00627 | 2/2000 |
| WO | WO 00/06026 | 2/2000 |
| WO | WO 00/06028 | 2/2000 |
| WO | WO 00/16700 | 3/2000 |
| WO | WO 00/18320 | 4/2000 |
| WO | WO 00/47270 | 8/2000 |
| WO | WO01/67985 | 2/2001 |
| WO | WO 01/28455 | 4/2001 |
| WO | WO 01/85061 | 11/2001 |
| WO | WO 01/91667 | 12/2001 |
| WO | WO 01/95830 | 12/2001 |
| WO | WO 01/95831 | 12/2001 |
| WO | WO 01/95832 | 12/2001 |

OTHER PUBLICATIONS

Melvin, D.B., "*Cardiovascular Surgery: Myocardial Preservation, Cardiorespiratory Support I,*", American Heart Assoc. Abstract, Circulation Part II, vol. 68, No. 4; Scientific Sessions for Nurses; 37th Ann. Meeting; Nov. 14-17, 1983.

Melvin, D.; Schima, H.; Losert, U.; Wolner, E., "*Long-Term Ventricular Wall Actuation: Can and Should it be Systematically Explored?*", Artificial Organs, vol. 20, No. 1, 1996.

Mevin, D.B., et al., "*A Physical Analog of the Failing Left Ventricle for In Vitro Studies of Mechanical Wall Actuation*", Artificial Organs, vol. 20, No. 3, 1996.

Melvin, D.B. et al., "*Reduction of Ventricular Wall Tensile Stress by Geometric Remodeling Device*", ASAIO Journal (Abstract), vol. 45, No. 2 p. 166, Mar. 17, 1999.

Melvin, D.B. et al., "*Reduction of Ventricular Wall Tensile Stress by Geometric Remodeling Device*", ASAIO Annual Meeting (Poster), Jun. 1999.

Melvin, D.B. , "*Device-Induced Ventricular Geometric Remodeling: Appraisal of Critical Issues*", J. of Cardiac Surgery (Accepted for publication), Presented at the 3rd Symposium of the Soc. of Cardiac Volume Reduction, Apr. 9, 2000 in Osaka, Japan.

\* cited by examiner

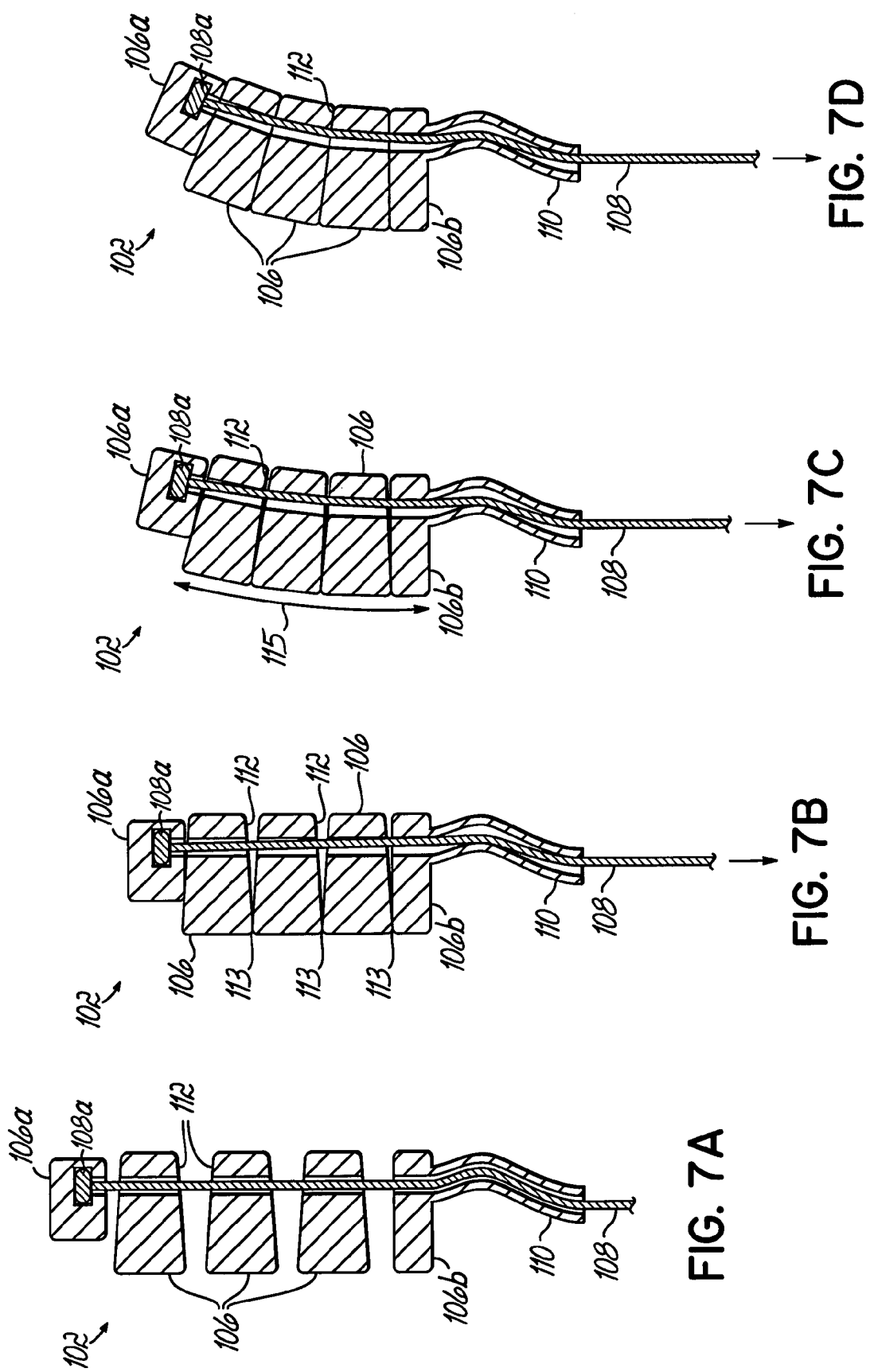

HEART WALL ACTUATION DEVICE FOR THE NATURAL HEART

RELATED APPLICATIONS

This application is a continuation application of U.S. patent application Ser. No. 09/850,554, filed May 7, 2001 (incorporated herein by reference), entitled "Heart Wall Actuation Device for the Natural Heart," now U.S. Pat. No. 6,592,619, which is a continuation-in-part application of U.S. patent application Ser. No. 09/326,416, filed Jun. 4, 1999 (incorporated herein by reference), entitled "Device and Method for Restructuring Heart Chamber Geometry," now U.S. Pat. No. 6,520,904, which is a continuation-in-part application of U.S. patent application Ser. No. 09/316,611, filed May 21, 1999 (incorporated herein by reference), entitled "Device and Method for Restructuring Heart Chamber Geometry," now abandoned, which is a continuation-in-part U.S. patent application Ser. No. 09/165,887, filed Sep. 30, 1998 (incorporated herein by reference), entitled "Device and Method for Restructuring Heart Chamber Geometry," now U.S. Pat. No. 6,221,103, which is a continuation-in-part U.S. patent application Ser. No. 08/581,914, filed Jan. 2, 1996 (incorporated herein by reference), entitled "Activation Device for the Natural Heart and Method of Doing the Same" (now U.S. Pat. No. 5,957,977), which is a continued prosecution application of U.S. patent application Ser. No. 08/581,914, filed on Jan. 2, 1996 (incorporated herein by reference).

FIELD OF THE INVENTION

This invention relates generally to assisting the natural heart in operation and, more specifically, to actuating a wall of the natural heart.

BACKGROUND OF THE INVENTION

The natural human heart and accompanying circulatory system are critical components of the human body and systematically provide the needed nutrients and oxygen for the body. As such, the proper operation of the circulatory system, and particularly, the proper operation of the heart, are critical in the overall health and well-being of a person. A physical ailment or condition which compromises the normal and healthy operation of the heart can therefore be particularly critical and may result in a condition which must be medically remedied.

Specifically, the natural heart, or rather the cardiac tissue of the heart, can fail for various reasons to a point where the heart can no longer provide sufficient circulation of blood for the body so that life can be maintained. To address the problem of a failing natural heart, solutions are offered to provide ways in which circulation of blood might be maintained.

Some solutions involve replacing the heart. Other solutions are directed to maintaining operation of the existing heart. One such solution has been to replace the existing natural heart in a patient with an artificial heart or a ventricular assist device. In using artificial hearts and/or assist devices, a particular problem stems from the fact that the materials used for the interior lining of the chambers of an artificial heart are in direct contact with the circulating blood. Such contact may enhance undesirable clotting of the blood, may cause a build-up of calcium, or may otherwise inhibit the blood's normal function. As a result, thromboembolism and hemolysis may occur. Additionally, the lining of an artificial heart or a ventricular assist device can crack, which inhibits performance, even when the crack is at a microscopic level. Moreover, these devices must be powered by a power source which may be cumbersome and/or external to the body. Such drawbacks have limited use of artificial heart devices to applications having too brief of a time period to provide a real lasting benefit to the patient.

An alternative procedure also involves replacement of the heart and includes a transplant of a heart from another human or animal into the patient. The transplant procedure requires removing an existing organ (i.e. the natural heart) from the patient for substitution with another organ (i.e. another natural heart) from another human, or potentially, from an animal. Before replacing an existing organ with another, the substitute organ must be "matched" to the recipient, which can be, at best, difficult, time consuming, and expensive to accomplish. Furthermore, even if the transplanted organ matches the recipient, a risk exists that the recipient's body will still reject the transplanted organ and attack it as a foreign object. Moreover, the number of potential donor hearts is far less than the number of patients in need of a natural heart transplant. Although use of animal hearts would lessen the problem of having fewer donors than recipients, there is an enhanced concern with respect to the rejection of the animal heart.

In an effort to continue use of the existing natural heart of a patient, other attempts have been made to wrap skeletal muscle tissue around the natural heart to use as an auxiliary contraction mechanism so that the heart may pump. As currently used, skeletal muscle cannot alone typically provide sufficient and sustained pumping power for maintaining circulation of blood through the circulatory system of the body. This is especially true for those patients with severe heart failure.

Another system developed for use with an existing heart for sustaining the circulatory function and pumping action of the heart, is an external bypass system, such as a cardiopulmonary (heart-lung) machine. Typically, bypass systems of this type are complex and large, and, as such, are limited to short term use, such as in an operating room during surgery, or when maintaining the circulation of a patient while awaiting receipt of a transplant heart. The size and complexity effectively prohibit use of bypass systems as a long term solution, as they are rarely portable devices. Furthermore, long term use of a heart-lung machine can damage the blood cells and blood borne products, resulting in post surgical complications such as bleeding, thromboembolism function, and increased risk of infection.

Still another solution for maintaining the existing natural heart as the pumping device involves enveloping a substantial portion of the natural heart, such as the entire left and right ventricles, with a pumping device for rhythmic compression. That is, the exterior wall surfaces of the heart are contacted and the heart walls are compressed to change the volume of the heart and thereby pump blood out of the chambers. Although somewhat effective as a short term treatment, the pumping device has not been suitable for long term use. Typically, with such compression devices, a vacuum pressure is needed to overcome cardiac tissue/wall stiffness, so that the heart chambers can return to their original volume and refill with blood. This "active filling" of the chambers with blood limits the ability of the pumping device to respond to the need for adjustments in the blood volume pumped through the natural heart, and can adversely affect the circulation of blood to the coronary arteries. Furthermore, natural heart valves between the chambers of the heart and leaching into and out of the heart are quite sensitive to wall and annular distortion. The movement patterns that reduce a chamber's volume and distort the heart walls may not necessarily facilitate valve closure (which can lead to valve leakage).

Therefore, mechanical pumping of the heart, such as through mechanical compression of the ventricles, must address these issues and concerns in order to establish the efficacy of long term mechanical or mechanically assisted pumping. Specifically, the ventricles must rapidly and passively refill at low physiologic pressures, and the valve functions must be physiologically adequate. The myocardial blood flow of the heart also must not be impaired by the mechanical device. Still further, the left and right ventricle pressure independence must be maintained within the heart.

Another major obstacle with long term use of such pumping devices is the deleterious effect of forceful contact of different parts of the living internal heart surface (endocardium), one against another, due to lack of precise control of wall actuation. In certain cases, this coaptation of endocardium tissue is probably necessary for a device that encompasses both ventricles to produce independent output pressures from the left and right ventricles. However, it can compromise the integrity of the living endothelium.

Mechanical ventricular wall actuation has shown promise, despite the issues noted above. As such, devices have been invented for mechanically assisting the pumping function of the heart, and specifically for externally actuating a heart wall, such as a ventricular wall, to assist in such pumping functions.

Specifically, U.S. Pat. No. 5,957,977, from which priority is claimed and which is incorporated herein by reference in its entirety, discloses an actuation device for the natural heart utilizing internal and external support structures. That patent provides an internal and external framework mounted internally and externally with respect to the natural heart, and an actuator or activator mounted to the framework for providing cyclical forces to deform one or more walls of the heart, such as the left ventricular wall. The present invention further adds to the art of U.S. Pat. No. 5,957,977 and specifically sets forth various embodiments of activators or actuator devices which are suitable for deforming the heart walls and supplementing and/or providing the pumping function for the natural heart.

Accordingly, it is an objective of the present invention to provide a device and method for actively assisting the natural human heart in its operation.

It is still another objective of the present invention to actuate and assist the heart at a proper natural rate in a way suitable for long term usage.

It is another objective of the present invention to assist the heart while allowing one or more of the heart chambers to rapidly and passively refill at low pressure after the actuating device has completed an actuation stroke.

It is a further objective of the present invention to do so while providing different independent pressures on the left and right side of the natural heart.

It is a still further objective of the invention to assist the heart in a way which minimizes damage to the coronary circulation and the lining tissue or endocardium of the heart.

It is another objective of the present invention to assist the heart while maintaining the competence of the heart valves in their natural function.

These objectives and other objectives and advantages of the present invention will be set forth and will become more apparent in the description of the invention below.

SUMMARY OF THE INVENTION

The present invention addresses the above objectives and other objectives, and provides an actuation system for assisting the operation of the natural heart. The actuation system comprises a framework for interfacing with the natural heart. The framework includes one or more internal framework elements which are configured to be positioned within the interior volume of a heart. The framework further includes one or more external framework elements which are configured to be proximate an exterior surface of the heart. The internal and external framework elements are coupled together to form a structure which cooperates with the heart. In one embodiment, the external framework elements are coupled proximate the chamber of the heart and along the wall or walls of that chamber or chambers which are to be actuated in accordance with the principles of the present invention.

An actuator system is coupled to the framework and is configured to engage an exterior surface of the heart. For example, if the left ventricle of the heart is to be actuated utilizing the invention, the external framework element will be positioned proximate to the left ventricle exterior wall, and then the actuator system will be similarly positioned. The actuator system comprises an actuator band extending along a portion of the heart wall exterior surface. The actuator band is selectively movable between an actuated state and a relaxed state, and is operable, when in the actuated state, to assume a predetermined shape or curvature, and thereby indent a portion of the heart wall to effect a reduction in the volume of the heart, and specifically a reduction in one of the chambers of the heart, for assisting the heart in its pumping function.

In one embodiment of the invention, the actuator band includes a plurality of juxtaposed elements, such as blocks, which are coupled together by one or more actuator cords. The blocks are configured to be drawn together when the actuator band is in the actuated state, and to cooperate, with each other, when drawn together, to assume the predetermined shape or curvature. The one or more cords which couple the blocks together are coupled to a drive apparatus to be moved by that apparatus and draw the blocks together to achieve such predetermined shape. The blocks have adjacent cooperating surfaces which are at least partially coextensive with each other when the blocks are drawn together in the actuated state. The actuator band is coupled or fixed at one or both of its ends to the external framework element and the drive apparatus is operable for selectively moving the actuator band between the relaxed and actuated states to achieve the desired assistance of the natural heart. In accordance with another aspect of the present invention, one or more curvature limiting devices, such as curvature limiting bands, are coupled to the actuator band. The curvature limiting bands limit the predetermined shape or curvature that may be imposed by the actuator band, on the heart surface—at the actuator band edges, at the yoke edges, or elsewhere, when it is in the actuated state in order to reduce the severity of the indentation against the actuated portion of the heart wall. In that way, the heart wall is shaped, and the volume of the heart is changed in a less severe manner which will limit the stress on the heart wall and heart. Preferably, the curvature limiting bands are operable for limiting the curvature imposed on any part of the external heart wall to a certain measurable degree of the natural relaxed and distended curvature of the heart wall, along which the actuator band extends. When the actuator band is in the relaxed state, it is operable to generally assume the natural curve of the distended, relaxed heart wall and does not offer resistance to the refilling of the heart, such that active filling of the heart chambers may be avoided.

In another aspect of the present invention, a paving surface might be positioned between the epicardium, or exterior surface of the heart, and the actuator band in order to provide smoother actuation and less damage to the epicardium.

In another embodiment of the invention, multiple actuator bands are utilized in combination with multiple curvature limiting bands, for actuating the heart at several positions along an exterior wall surface.

The drive apparatus of the invention is positioned remotely from the framework, heart and actuator band, and is coupled to the band through one or more cords which couple the elements or blocks together. In that way, the actuator band may be actuated remotely from the heart. One such drive apparatus utilizes a solenoid which is coupled to the one or more cords and selectively moves those chords to selectively move the actuator band between the actuated and relaxed states. Preferably, an energy storing device, such as a spring or elastic element is coupled between the armature or plunger of the solenoid and the cords. In that way, upon movement of the solenoid, the actuator band is moved more gradually to the actuated state from the relaxed state to further reduce the immediate stress to the heart wall and heart. The remote drive apparatus may be surgically positioned in the body at a site which is readily accessible, and particularly more accessible than the chest cavity and the heart. In that way, the drive system may be adapted, repaired, or upgraded, without the invasiveness of cardiothoracic surgery. The drive system will include one or more energy-providing elements for operating the solenoid or other drive elements of the apparatus. Further details of the invention are set forth hereinbelow in the drawings and detailed description.

BRIEF DESCRIPTION OF THE DRAWINGS

The accompanying drawings, which are incorporated in and constitute a part of this specification, illustrate embodiments of the invention and, together with a general description of the invention given below, serve to explain the principles of the invention.

FIGS. 7A-7D illustrate another sectional view of an actuator band showing the progression of the actuator band between the relaxed state and the actuated state.

DETAILED DESCRIPTION

The present invention may best be described in the context of the natural human heart, and accordingly, the heart structure is discussed briefly below. Furthermore, the actuator system of the invention, in one embodiment, is coupled to a framework which cooperates with the human heart. One suitable framework for practicing the invention is disclosed in U.S. Pat. No. 5,957,977, to which priority is claimed, and which is incorporated herein by reference. Other frameworks may also be suitable. A brief overview of the framework of U.S. Pat. No. 5,957,977 is also set forth herein.

Figure 1:
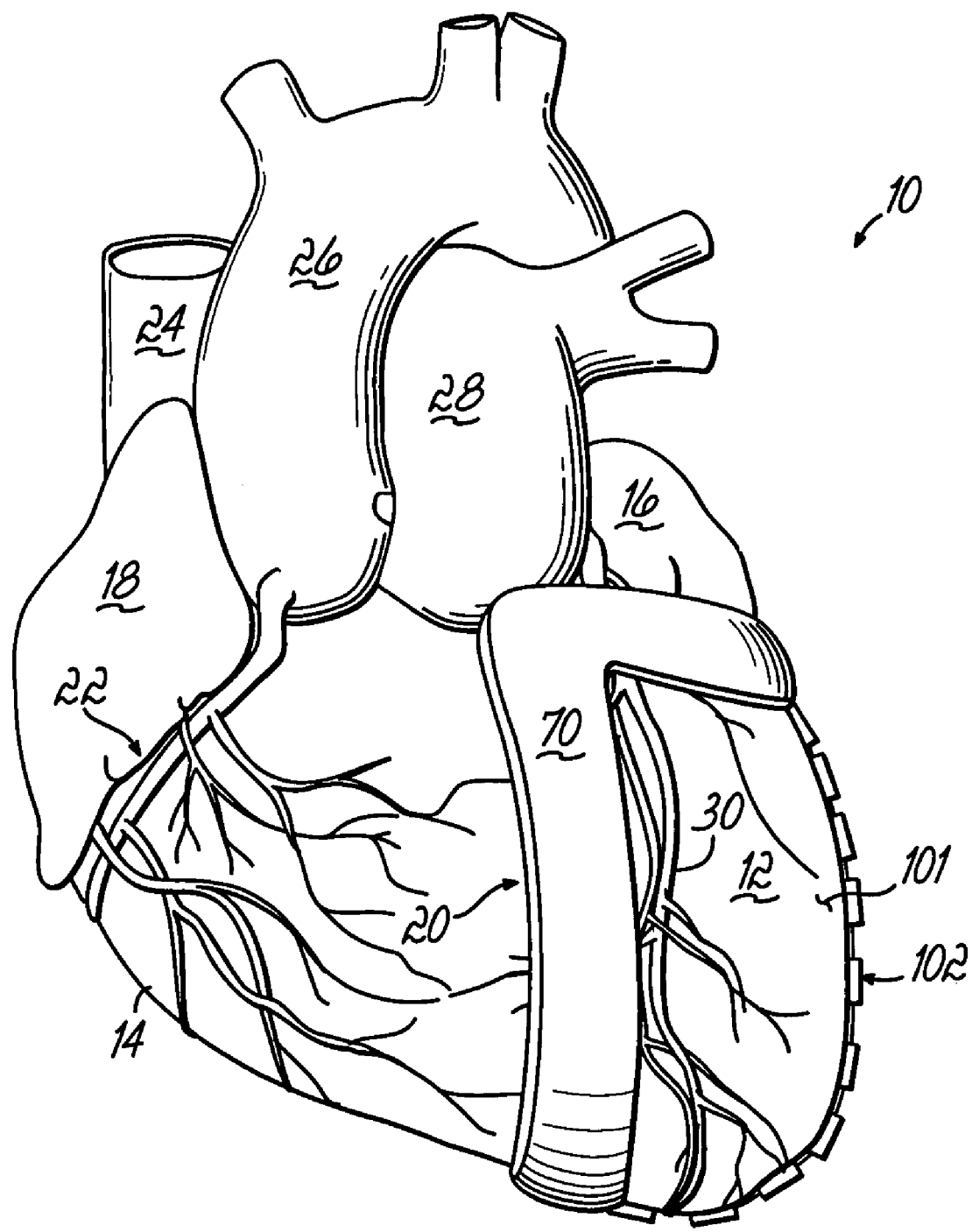
FIG. 1 is a perspective view of one embodiment of the invention illustrated on a natural human heart.

Referring now to FIG. 1, a natural human heart 10 is shown in perspective with a portion of the framework of the actuation system, and has a lower portion comprising two chambers, namely a left ventricle 12 and a right ventricle 14, which function primarily to supply the main pumping forces that propel blood through the circulatory system, including the pulmonary system (lungs) and the rest of the body, respectively. Heart 10 also includes an upper portion having two chambers, a left atrium 16 and a right atrium 18, which primarily serve as entryways to the ventricles 12 or 14, and also assist in moving blood into the ventricles 12 or 14. The interventricular wall or septum of cardiac tissue separating the left and right ventricles 12 and 14, is defined externally by an interventricular groove 20 on the exterior wall of the natural heart 10. The atrioventricular wall of cardiac tissue separating the lower ventricular region from the upper atrial region is defined by atrioventricular groove 22 on the exterior wall of the natural heart 10. The configuration and function of the heart is known to those skilled in this art.

Generally, the ventricles are in fluid communication with their respective atria through an atrioventricular valve in the interior volume defined by heart 10. More specifically, the left ventricle 12 is in fluid communication with the left atrium 16 through the mitral valve, while the right ventricle 14 is in fluid communication with the right atrium 18 through the tricuspid valve. Generally, the ventricles are in fluid communication with the circulatory system (i.e., the pulmonary and peripheral circulatory system) through semilunar valves. More specifically, the left ventricle 12 is in fluid communication with the aorta 26 of the peripheral circulatory system, through the aortic valve, while the right ventricle 14 is in fluid communication with the pulmonary artery 28 of the pulmonary, circulatory system through the pulmonic or pulmonary valve.

The heart basically acts like a pump. The left and right ventricles are separate, but share a common wall, or septum. The left ventricle has thicker walls and pumps blood into the systemic circulation of the body. The pumping action of the left ventricle is more forceful than that of the right ventricle, and the associated pressure achieved within the left ventricle is also greater than in the right ventricle. The right ventricle pumps blood into the pulmonary circulation, including the lungs. During operation, the left ventricle fills with blood in the portion of the cardiac cycle referred to as diastole. The left ventricle then ejects any blood in the part of the cardiac cycle referred to as systole. The volume of the left ventricle is largest during diastole, and smallest during systole. The heart chambers, particularly the ventricles, change in volume during pumping. It is this feature to which the present invention is directed.

By way of a non-limiting example, the present invention is discussed in terms of embodiments that are used to primarily assist in the actuation and operation solely of the left ventricular portion of the heart 10. However, it is noted that the present invention can also be used to assist in the actuation and operation of other portions of the natural heart 10, such as individual atria, of the right ventricular portion of the heart 10, or simultaneously both atria or both ventricles.

In accordance with illustrating an example of use of the invention with the left ventricular portion of the heart, a framework is discussed which positions an actuator system on the exterior surface or epicardium of the left ventricle. The framework might also be used for other sections of the heart.

Figure 2:
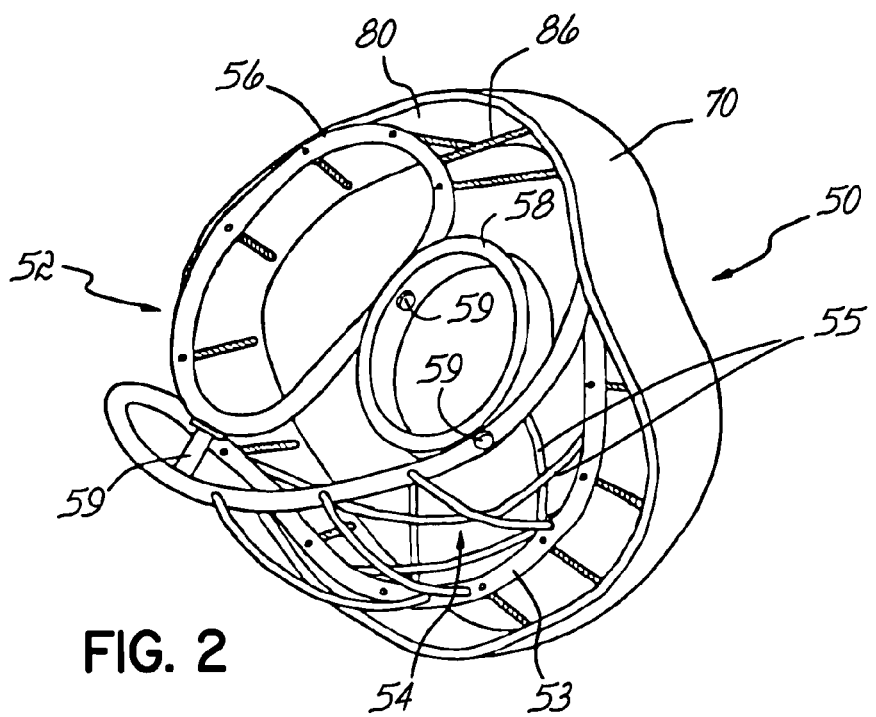
FIG. 2 is a perspective view of a framework for interfacing with the natural heart in accordance with one aspect of the present invention.

The framework is generally illustrated in FIG. 2 by reference numeral 50, which includes internal framework elements including an internal stint 52 and an external yoke or external framework element 70 fixed to the internal stint 52 by transmural cords 86 which extend through walls of the heart. The internal stint 52 is sized and configured for placement within the interior volume of the natural heart 10, generally alongside the right side of the interventricular septum. The stint 52 includes a generally triangular shaped frame 53 that can be assembled from a plurality of interlocking struts, or may be made of a single piece, part or all of which is flexible. The stint 52 also includes at least two separate ring structures for positioning proximate the valve annuli of the left side of the heart. A first ring 56 is sized and configured for placement adjacent the atrioventricular valve annulus, and preferably suprajacent the mitral valve annulus in the left atrium 16. A second ring 58 is sized and configured for placement adjacent the semilunar valve annuli, preferably subjacent the aortic valve annuli in the left ventricle 12.

FIG. 2 further illustrates a septal splint 54 which can include one or more strands of sutures (e.g., 55) affixed to the frame 53 through loops positioned on the frame 53, preferably the loops are affixed to the inner portion of frame 53, and more preferably at about 1.5 cm intervals. The splint 54 can take the form of a tennis racket-like shaped configuration, or a snowshoe-like shaped configuration to brace or stabilize one side of the septum of the heart, without distortion of the chordae structures of the heart. The septal splint 54 may be positioned by stringing a heavy monofilament polypropylene suture, such as a #5 polypropylene suture, under, through, and behind the trabeculae, and through the loops, as discussed in greater detail in U.S. Pat. No. 5,957,977. Alternatively, a heavy, loosely braided, multifilament, polyester with total cross-sectional area approximately that of a #4 or #5 suture may be used. The first and second rings 56 and 58 and the septal splint 54 are attached at least to each other using connectors 59, (e.g. pins or other flexible or rigid connectors) to assist in maintaining the relative position so that the first and second rings, 56 and 58 respectively, and the splint 54 are supported while the natural heart is being actuated in accordance with the invention. It is desirable that the connection of the components is semi-rigid or springlike to reduce stress and material fatigue of the components.

So that the components of the stint 52 (e.g., the septal splint 54 and first and second rings 56 and 58) are not totally rigid and can exhibit an elastic quality, the components are preferably made of a stiff coil spring material covered with braided polyester. Localized adjustments can be made to the elasticity of the various components of the stint 52 to reduce the potential for problems, such as damaging the cardiac tissue or compromising the coronary circulation or inducing excessive material stress concentration in the components themselves.

In one embodiment, the spring/fabric structures used for the stint components are filled or impregnated with a soft elastomer, such as a biocompatible silicone rubber or a polyurethane. The internal surfaces which contact blood or tissue are made of an open-structured, porous, biocompatible polymer, such as polyester velour, loosely braided polyester fiber, and/or expanded polytetrafluoroethylene (ePTFE). Alternatively, some segments of the stint—either the valve rings or the septal splint—may be flexible, for example, incorporating sections of braided polymer cord 2 to 5 mm in diameter.

As illustrated in FIG. 2, the framework 50 also includes an external element, such as yoke 70, for placement around a portion of the exterior surface or epicardium of a natural heart 10. The generally stirrup-shaped yoke 70 in the illustrated embodiment restricts free motion of the natural heart 10 so that the natural heart 10 can be actuated and assisted. Yoke 70 also acts as an anchor for the actuator system of the invention. Preferably, the yoke 70 is between about 1 and 2 cm wide and includes a semi-rigid collar portion, preferably made of either a solid polymer of appropriate mechanical behavior, such as polypropylene or polyacetal, or a composite of metal (stainless steel or pure titanium) band or coil spring elements, polymer fabric and fiber (e.g. polyester knit) and soft elastomer, for providing rigidity to the yoke 70. Additionally, the yoke 70 may include a gel-filled cushion portion 80 that is positioned immediately adjacent the exterior surface (epicardium) of the natural heart 10 for providing equalized pressure over the irregularities in the epicardial surface of the heart 10, and any of the coronary arteries 30 within a region under the yoke 70. Preferably, the yoke 70 is sized and configured for placement adjacent at least a portion of the atrioventricular groove 22, and simultaneously adjacent at least a portion of the anterior and posterior portions of the interventricular groove 20, and most preferably, adjacent at least a substantial portion of the anterior and posterior portion of the interventricular groove 20, as shown in FIG. 1.

General alignment of the yoke 70 with interior framework elements is maintained by at least one transmural cord 86, and preferably, a plurality of cords 86 that penetrate the walls of the natural heart 10 and connect to the stint 52 and one or more of the rings 56, 58. The cords 86 are preferably made of a heavy braided, polymer-impregnated polyester suture core (such as #5 Ethibond® by Ethicon, Inc.), covered in the intermyocardial portion of the heart with a braided sleeve of polyester yarn to promote firm tissue growth around the cord 86. When it is necessary to utilize more than one cord 86 with the present invention, spacing of the cords 86 should preferably be at intervals of between about 15 mm to 20 mm along the yoke 70, from the septal splint 54 and the first ring 56 extending obliquely outwardly toward the left ventricle exterior wall for insertion into the yoke 70. More preferably, the cords 86 should be positioned for avoiding contact with the coronary vessels 30.

Figure 3A:
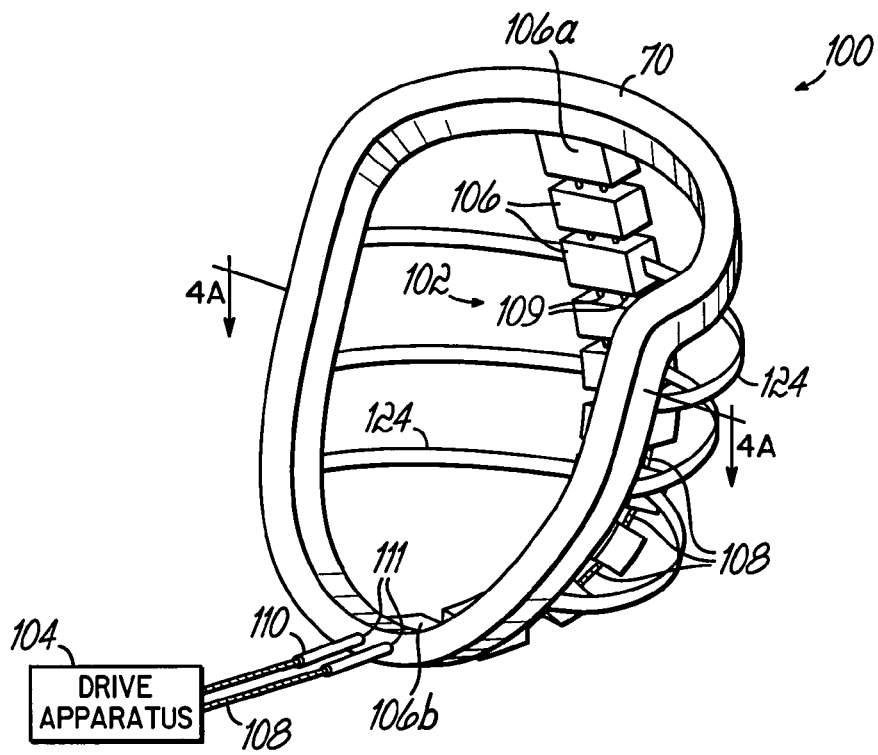
FIGS. 3A and 3B illustrate perspective views of an embodiment of the invention in the relaxed and actuated states, respectively.
Figure 3B:
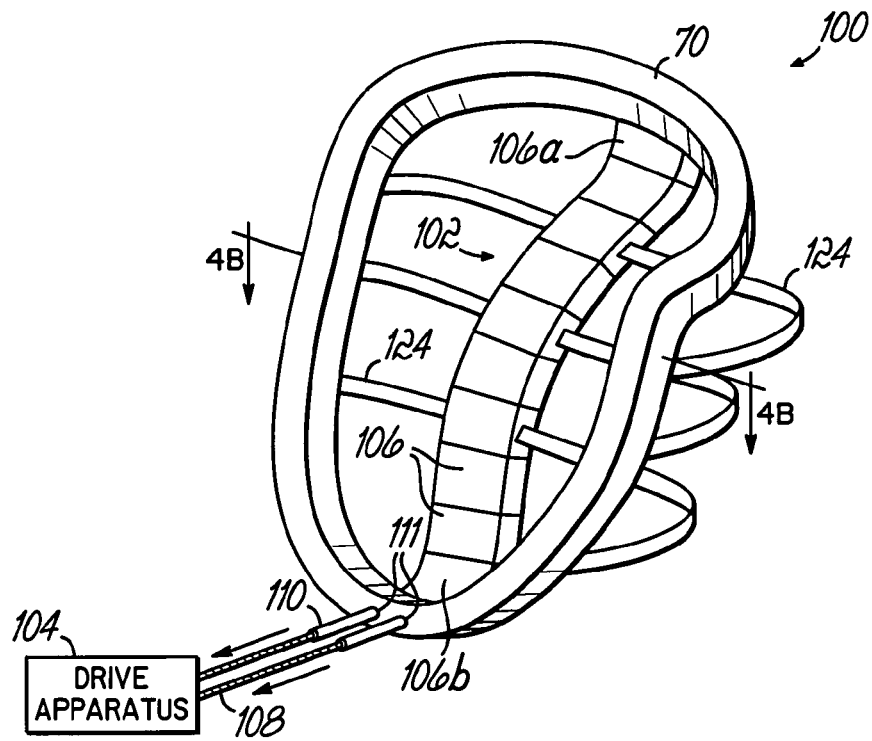

FIGS. 3A and 3B illustrate one embodiment of the present invention which may be coupled to the framework described above, and specifically to the external framework element or yoke 70. The actuator system 100 of the invention is configured to engage a heart wall exterior surface, or epicardial surface 101 of the heart 10 (See FIGS. 4A, 4B, and 5A, 5B). The actuator system 100 has a relaxed state as illustrated in FIG. 3A, wherein the actuator band 102 of the actuator system will generally follow the distended curvature of the relaxed or diastolic heart. The actuator system also has an actuated state, as illustrated in FIG. 3B, wherein it engages the outer surface of the heart and effects a shape and volume change of a portion of the heart, such as the left ventricle. In the embodiment of the invention illustrated in FIGS. 3A and 3B, the actuator system comprises an actuator band 102 which is selectively movable between the actuated state (FIG. 3B) and relaxed state (FIG. 3A). The actuator band 102 is operable, when in the actuated state, to assume a predetermined shape and/or curvature, and thereby indent a portion of the heart wall to effect a reduction in the volume of the heart. A drive apparatus 104 is coupled to the actuator band and is operable for selectively moving the actuator band between the relaxed and actuated states to achieve the desired assistance of the natural heart.

Figure 4A:
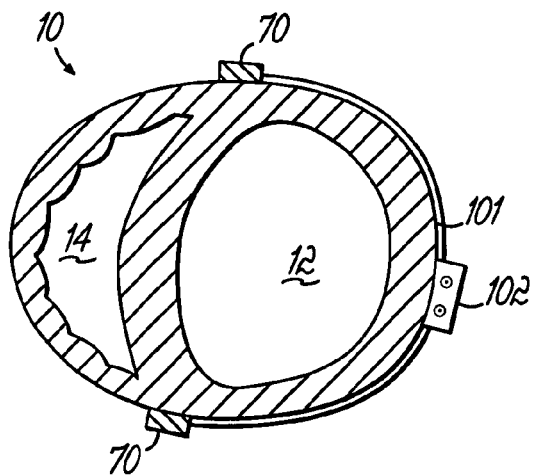
FIGS. 4A and 4B are cross-sectional views along lines 4A-4A and 4B-4B of FIGS. 3A and 3B.
Figure 4B:
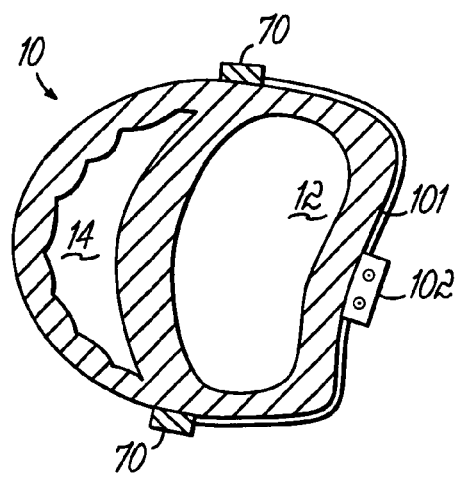

Referring now to FIGS. 4A and 4B, a cross-sectional view generally along the lines 4A-4A and 4B-4B is shown with the yoke 70 and actuator band 102 coupled to a heart 10. Referring to FIG. 4A, the actuator band is in a relaxed state, and the band 102 generally follows the extended or distended shape of the heart in the diastolic portion of the cardiac cycle. FIGS. 4A and 4B illustrate the band 102 against the exterior wall surface of the left ventricle 12. The actuator band is coupled at its ends to the yoke 70 such that when it is in the actuated state, it presses in the heart wall to change the shape and volume of the heart, particularly to change the shape and volume of the left ventricle 12, as illustrated in FIG. 4B. The drive system 104 is preferably operable to cyclically move the actuator band 102 between the relaxed and actuated states in accordance with the principles of the present invention.

In one embodiment of the invention, the actuator band 102 includes a plurality of juxtaposed elements, such as in the form of blocks 106, which are configured to be drawn together when the band is in the actuated state. The band elements, when drawn together when the band is in the actuated state, cooperate with each other so that the complete band assumes a predetermined shape, as illustrated in FIG. 3B. That shape provides the desired shaping of a portion of the heart, such as the left ventricle (see FIG. 4B). In the illustrated embodiment, the blocks 106 are coupled together by one or more actuator cords 108. The cords and blocks slide or move with respect to each other. The cords in the figures are shown to extend through apertures 109 formed in the blocks. Alternatively, the cords might extend through channels formed in the blocks, such that the blocks do not completely enclose the cords.

To move band 102 to the actuated state, the drive apparatus 104 draws the cords 108, and generally shortens the cords with respect to the ends of the band 102. The cords slide through the blocks. The cords also slide or move within a sheath 110 coupled between the band 102 and drive apparatus 104. Shortening the cord and pulling it through the blocks 106 and sheath 110 moves the blocks together to form the shortest distance between the ends of the band which is defined by the blocks. The sheath is anchored at the framework 52 and at the drive apparatus. Such a cable/sheath assembly is referred to as a Bowden cable assembly and provides mechanical actuation from a remote drive apparatus. The blocks slide or move with respect to the cords, and thereby come together to adapt to the shortened length of the cords between the ends of the band. To couple the actuator band with the yoke 70 of the framework, one or more of the blocks 106 may be fixed to the yoke 70 or movably coupled with respect to the yoke.

Figure 6A:
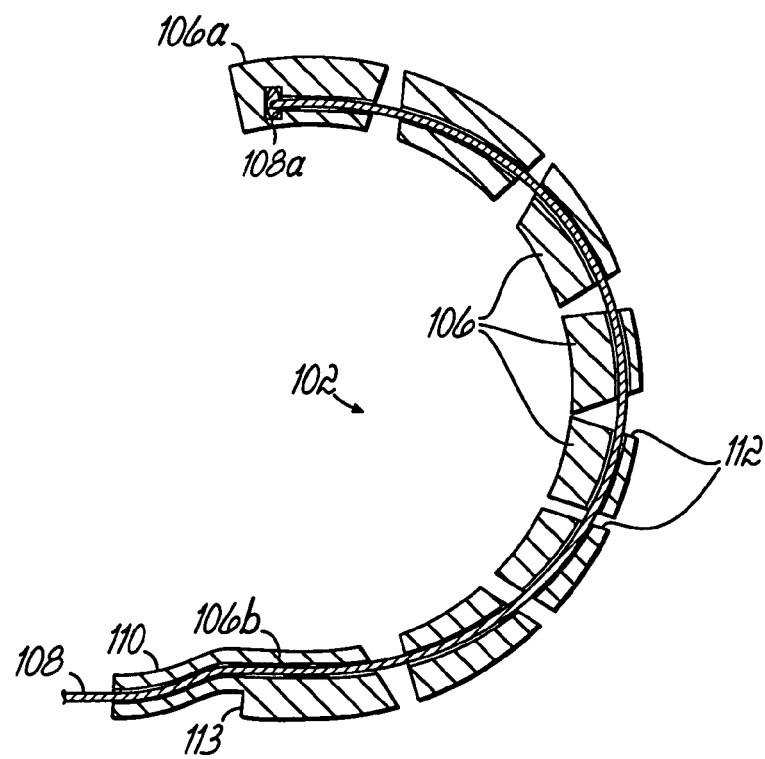
FIGS. 6A and 6B illustrate a sectional view of an actuator band in the relaxed and actuated states, respectively.
Figure 6B:
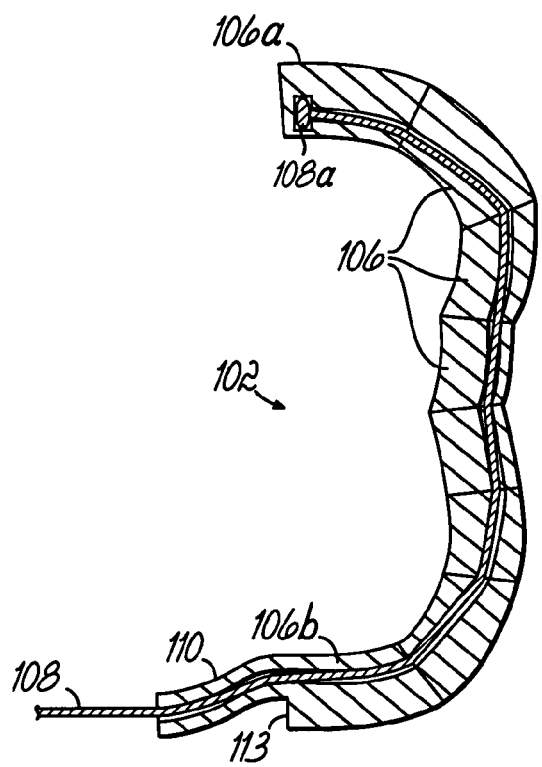

Referring to the FIGS. 6A and 6B, one embodiment of the actuator band 102 is illustrated in cross-section, showing the cooperation of the blocks 106 in the actuated state to make the band 102 form a predetermined shape. When in the actuated state, the band exerts a lateral force on the heart wall at local positions, and thereby deforms the heart wall to a predetermined shape to change the volume and shape of the heart chambers (see FIG. 4B). The precise shape assumed by the heart and its chambers, based upon the actuator band 102 will be determined by the balance of the forces created by the band, and the heart wall forces, as well as inertial forces associated with both.

One or more of the blocks 106 may be fixed to yoke 70 while other blocks are movable with respect to yoke 70. In FIGS. 3A and 3B, block 106a is fixed to an upper portion of the yoke 70. Another end block 106b is coupled to the sheaths or sleeves 110, through which the cords 108 move. The sheaths 110 may be formed as part of the block 106b as shown in FIGS. 6A, 6B. The sheaths 110 would then extend through suitable apertures 111 formed within the yoke 70. Alternatively, the sheaths may be integrally formed with yoke 70. The sheaths 110 might be fixed to yoke 70 or may move proximate yoke 70. Therefore, block 106b may be movably coupled with respect to the yoke 70, as the sheaths 110 may slide in the apertures 111.

FIGS. 6A and 6B illustrate a side cross-sectional view of the band 102. Each of the blocks 106 has side surfaces 112 which are juxtaposed with the similar side surfaces 112 of adjacent blocks. The side surfaces 112 are appropriately shaped and angled to cooperate when the drive system draws and puts tension on the cord 108 to draw the blocks 106 together. Depending upon the angle or shape of the block face surfaces 112, the band 102 will assume a predetermined shape, as illustrated in FIG. 6B. Block 106a is fixed to the yoke 70, and also fixes one end of cord 108. In that way, when the drive apparatus draws or puts tension on cord 108, the effective length of the cord between end blocks 106a and 106b is shortened. Although end block 106b moves with respect to the yoke 70, it will eventually move against the yoke and thereby fix the other end of the band 102 in position. For example, a shoulder 113 formed on block 106b will abut against a surface of the yoke when the cord is tensioned. Of course, block 106b might also be fixed to yoke 70. As the tensioned cord 108 between the end blocks 106a and 106b is shortened, the blocks will be drawn together such that the surfaces 112 become coextensive and define a continuous band with a predetermined shape of the actuated band 102. As shown in the Figures, the cord 108 slides freely through apertures 109 formed in the blocks 106.

When the drive apparatus is operated to move the actuator band to the relaxed state, tension on cord 108 is released, the cord may extend and the blocks are free to again slide with respect to the cord so that the band takes the shape of the distended heart and outer surface 101 during the diastolic portion of the cardiac cycle. The band in the relaxed state does not offer significant inertia to the shape of the diastolic heart.

FIGS. 7A-7D illustrate a more gradual change in the spacing between the blocks 106 and the shape of the actuator band 102 when it is moved between the relaxed state and the actuated state by placing tension on cord 108. Specifically, referring to FIG. 7A, the band 102 in the relaxed state is shown wherein the section of the cord 108 between the end blocks 106a and 106b is generally at its longest length so the blocks of band 102 are separated and freely conform to the distended diastolic heart. Spaces exist between the blocks 106, and the surfaces 112 are generally not touching, and at least are not coextensive with each other or forced together. FIG. 7A shows the band 102 in a relaxed state, and it will follow the shape of the distended heart wall exterior on which it lays.

During actuation, the drive apparatus introduces tension on cord 108 to thereby shorten its effective length between the end blocks 106a and 106b. As noted, the position of the blocks 106a and 106b is set by the yoke 70. As cord 108 is drawn, its length between the end blocks 106a, 106b is shortened, thereby drawing the blocks 106 together. As illustrated in FIG. 7B, at points 113, the shaped side surfaces 112 of the blocks begin to touch. However, the band has not yet taken its predetermined shape. Referring to FIG. 7C, as the cord 108 is drawn with greater tension and its effective length along the actuator band 102 is shortened, the blocks are drawn further closer together, such that the shaped surfaces begin to become more coextensive position. Depending upon the angle or shape of the surfaces 112, the blocks begin to define the overall shape of the band. That is, referring to FIG. 7C, the band begins to take a predetermined shape or curve, as illustrated by reference arrow 115. Finally, as illustrated in FIG. 7D, the blocks 106 are drawn together such that the surfaces 112 are at their most coextensive point, and the band 102 has achieved its desired predetermined curvature or shape. During the changing shape of band 102, the forces are exerted by the band on the heart wall to vary the shape of the heart and its chambers. In that way, the present invention may cyclically actuate or assist the heart in its pumping functions.

Generally, FIG. 7A corresponds to FIG. 4A, showing the band 102 in the relaxed state with the heart distended and thereby defining the shape of the band. FIG. 7D corresponds to FIG. 4B wherein the band 102 is in its fully actuated stated, thereby deforming the wall of the heart 10, as shown.

In the embodiments illustrated in FIGS. 6A-6B, and 7A-7D, cord 108 is fixed with respect to its one end. As illustrated, the end of the cord which interfaces with the block 106a may include a collar or head 108a which engages an appropriately formed cavity in the block 106a for securing the end of the cord with respect to the block. Therefore, the cord and its relative position does not change with respect to block 106a while its position does change with respect to the other blocks 106, including block 106b.

Figure 8A:
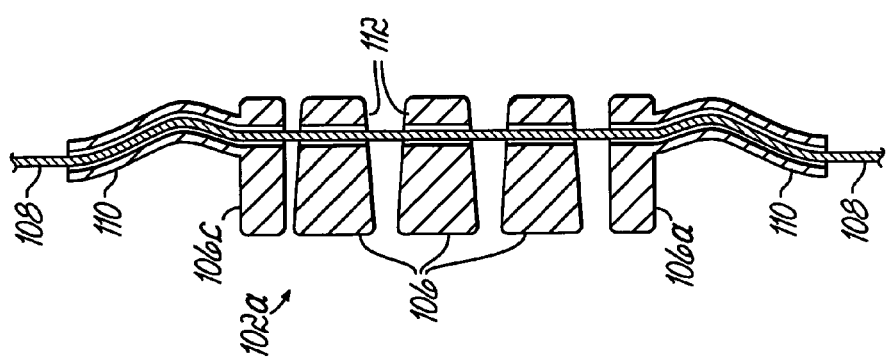
FIGS. 8A and 8B illustrate a sectional view of an alternative embodiment of the actuator band of the invention in the relaxed and actuated states, respectively.
Figure 8B:
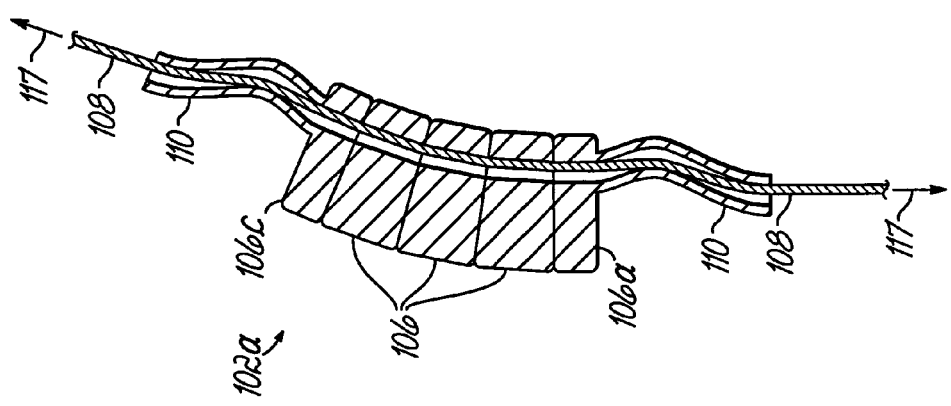

In FIGS. 8A and 8B, an alternative embodiment of the band 102a is illustrated in which cord 108 may move with respect to both end blocks. Specifically, the end block 106c may resemble the end block 106a such that the cord 108 moves with respect to all of the blocks of the band 102a. FIG. 8B illustrates band 102a in an actuated state. Band 102a may be placed in that actuated state by movement of the cord 108 in either direction, as illustrated by reference arrows 117. Generally, tension will be introduced on both ends of cord 108 simultaneously, or one of the ends will be selectively fixed for moving band 102a to the actuated state.

The embodiments discussed in FIGS. 6A, 6B, 7A-7D, and 8A-8B all illustrate tension on a single cord 108. However, as illustrated in FIGS. 3A and 3B, multiple cords 108 might be utilized for coupling the blocks 106 together and placing the band in the actuated state.

Figure 9:
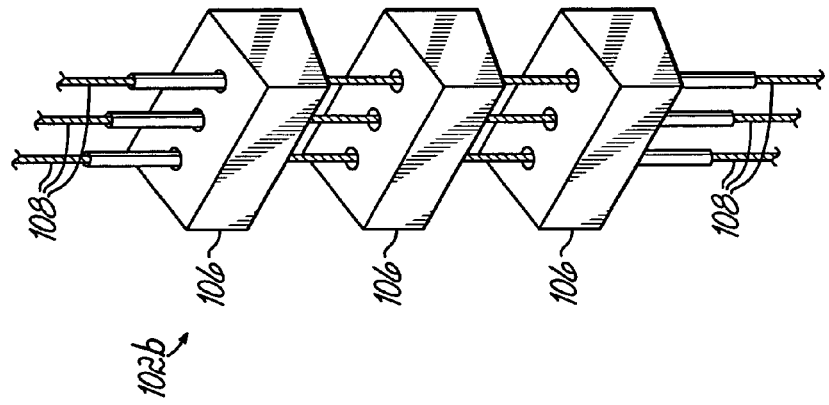
FIG. 9 illustrates an alternative embodiment of the actuator band of the invention.

Furthermore, FIG. 9 illustrates another embodiment wherein 3 cords 108 are utilized. FIG. 9 illustrates an alternative band 102b in the relaxed state. Accordingly, the present invention is not limited by the number of cords which might be utilized to position the blocks together so that the band forms a predetermined shape against a heart wall.

Figure 5A:
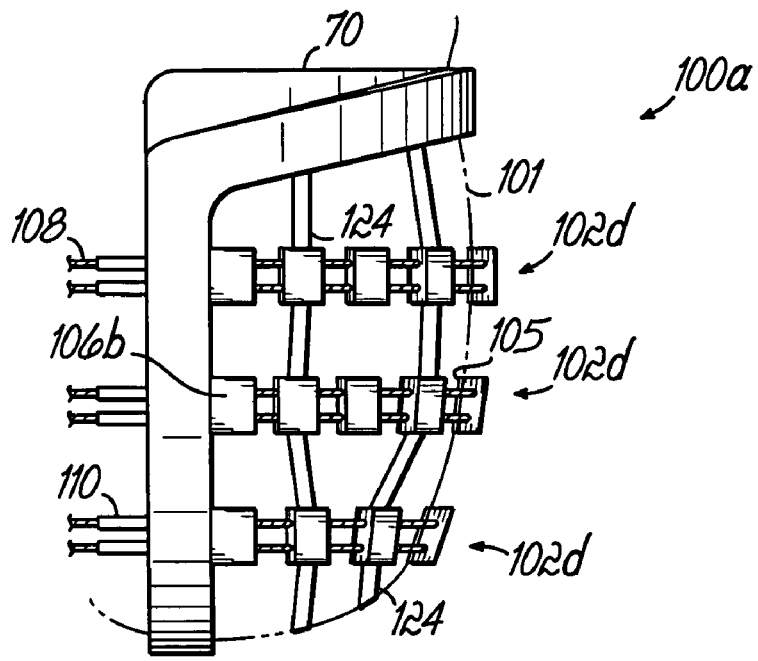
FIGS. 5A and 5B illustrate an alternative embodiment of the invention in the relaxed and actuated states, respectively.
Figure 5B:
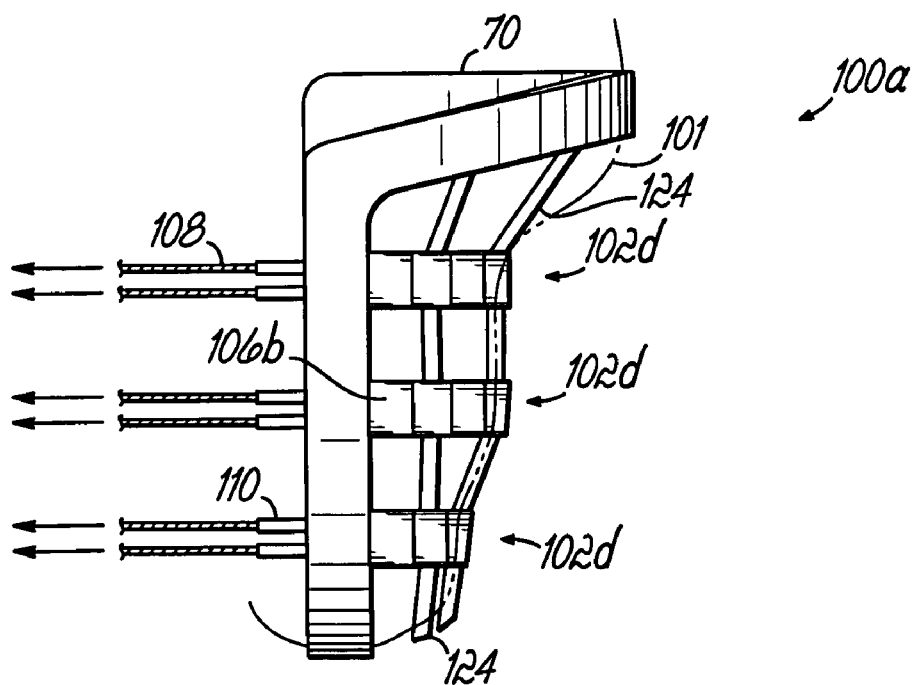

In accordance with another aspect of the present invention, the actuator system might include multiple actuator bands which extend along a portion of a heart wall exterior surface at different positions. FIGS. 5A and 5B illustrate an alternative embodiment of the invention utilizing three actuator bands. In the embodiment of FIGS. 3A and 3B, the actuator band is coupled generally to the top and bottom of the yoke 70, and extends generally vertically. Alternatively, the bands 102d extend transversely and generally horizontally across the yoke 70. Bands 102d include a plurality of juxtaposed elements, such as blocks 106, which are configured to be drawn together in the actuated state and to cooperate with each other, when drawn together to assume the predetermined shape of the band.

FIGS. 5A and 5B illustrate the actuator system 100a positioned to engage an exterior surface of the heart. FIG. 5A illustrates the various bands 102d in relaxed states, and FIG. 5B illustrates the bands in the actuated state, thereby indenting different portions of the heart wall 101 to effect a reduction in the volume of the heart. Like the embodiments discussed with respect to FIGS. 3A and 3B, each of the bands 102d may include blocks 106a, which are fixed to the yoke 70, and/or other end block 106b which are fixed or are movably coupled with respect to yoke 70. The bands include cords 108 which extend through respective sheaths 110.

The juxtaposed elements forming the actuator bands disclosed in the drawings take the form of six-sided blocks which cooperate to form a band assuming a predetermined shape. However, the elements might take other forms which will achieve the desired predetermined shape when the band is in the actuated state. Therefore, the present invention is not limited to the use of blocks having six generally planar sides.

The elements 106 are preferably formed of a material which is compatible with the body and specifically with the epicardial surface of heart 10, and also of demonstrated durability in applications requiring impact and friction with itself and with polished metal surfaces. For example, the blocks might be formed of pyrolytic carbon or polyacetal. At the point of contact between the elements 106 and the heart wall exterior surface, or epicardium 101, the natural heart may form a fibrous surface with accompanying lubricating fluid in response to the physical contact of the actuator band with the living epicardium. The fibrous surface and fluid would thereby preferably allow stable continuous unimpaired function of the actuator band 102 against the exterior heart wall surface. Such an encapsulation process would be similar to the usually-observed tissue response to artificial joints, such as prosthetic knees and hip joints. If implantation of such devices is followed by regular motion, tissue does not grow into the space between articulating surfaces and thus limit free motion of the joint. Rather, given regular movement, a tough fibrous capsule forms to surround the junction of articulating parts, and a wetting amount of tissue fluid accumulates to provide an effective lubricant. The intrinsic continuous movement of the invention could reasonably be expected to stimulate a similar healing response process.

Alternatively, a separate paving membrane or element, illustrated by reference numeral 105 might be utilized with the actuator band to provide for smooth and unimpaired functioning of the band. The paving element or membrane 105 could be any suitable material which would allow the continuous and unimpaired function of the band without irritating the epicardial surface of the heart. The paving membrane should be flexible and porous so that it might be deformed by the action of the actuator system to, in turn, deform the heart wall. The forces of the actuator system would therefore be transmitted to the heart, and the paving membrane 105 will absorb the friction of movement of the band 102 to protect the heart surface from abrasion, pinching, or other trauma. For example, one suitable material for the paving membrane might be a covering of the heart surface by a mesh comprised of interlinked smooth stainless steel rings assembled in the fashion of chain mail armor. Another example might be a loosely knitted polymer fabric "sock" over the heart surface that is studded on its outer surface by rounded-surface buttons of polished biocompatible metal or polymer.

The cords 108 extending between the elements 106 may be any suitable cord-like structure, including a band, a cable, a chain, or other suitable structure. The cord structure might be formed of a suitable material for use inside the body, such as CP titanium and/or 316 stainless steel.

In several of the illustrated embodiments, the end elements 106a, 106b are fixed or movably coupled with the yoke. Alternatively, one or more of those elements might be integrally formed with the yoke. In the illustrated embodiments, the intermediate elements, or blocks, are freely movable with respect to the cords 108. Alternatively, one or more of those intermediate elements might be fixed to the yoke 70 either in addition to, or alternatively to the end blocks being fixed to the yoke. In another alternative, each of the end blocks might be fixed relative to each other, both as to an angular orientation and the distance between the blocks.

Figure 10A:
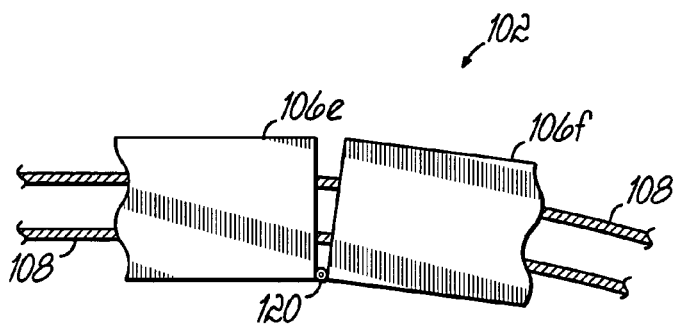
FIGS. 10a, 10b, and 10c illustrate other alternative embodiments of an actuator band of the present invention.
Figure 10B:
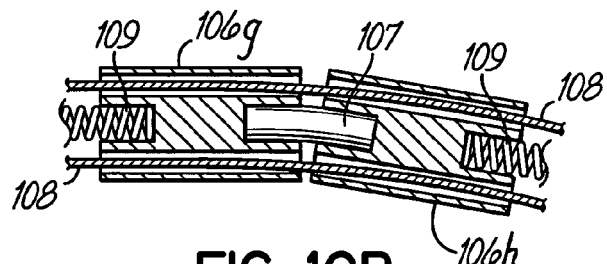
Figure 10C:
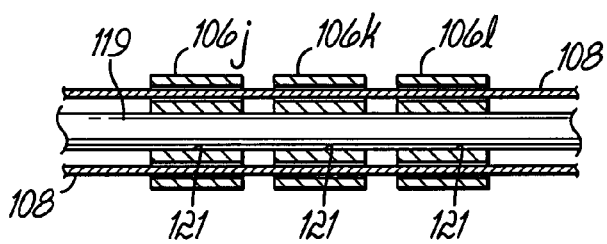

FIGS. 10a, 10b, and 10c illustrate other alternative embodiments of the invention wherein the actuator band includes a plurality of juxtaposed elements which are physically coupled to each other by an additional mechanism other than just the cords 108. Specifically, one or more of the elements, such as the blocks 106, forming the actuator band, may be physically coupled to an adjacent element. Referring to FIG. 10a, a block 106e is hingedly coupled to a block 106f through an appropriate hinge structure 120 such that the blocks 106e and 106f cannot pull completely apart from each other when the actuator band 102 is in a relaxed state. When the actuator band is in the actuated state, the tension on the cord 108 draws the blocks 106e and 106f together and they hinge together about the hinge structure 120 so the actuator band forms a predetermined shape, as desired.

Referring to FIG. 10b, blocks 106g and 106h are coupled together by a resilient member 107 which may be a coil spring, such as spring 109, shown in the Figure. Alternatively, the resilient member 107 might be some other device which allows the blocks to flex with respect to each other in accordance with the principles of the present invention.

FIG. 10c illustrates another embodiment wherein the blocks 106j, 106k and 106l have apertures 121 therethrough. A unitary resilient member 119 then extends through the apertures to couple the blocks together. When actuated, such as by cords 108, the embodiments of FIGS. 10a, 10b, and 10c assume a predetermined shape, as discussed above.

In accordance with another aspect of the present invention, the actuator band 102 may be coupled with one or more curvature limiting devices which limit the curvature or indentation of a portion of the heart wall caused by the predetermined shape of the actuator band.

Figure 11A:
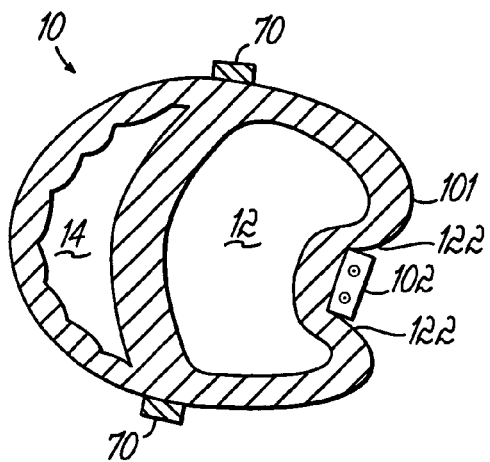
FIGS. 11A and 11B illustrate the operation of curvature limiting bands in accordance with one aspect of the present invention.

Specifically, when an actuator band in the actuated state engages a heart wall, its point or area of engagement may induce a sharp indentation in the heart wall 101, as illustrated in FIG. 11A. That is, based upon the forces supplied to the heart wall by the actuator band, the heart wall may take a different form or shape which includes steep indented walls 122 wherein portions of the heart wall are sharply distended between the actuator band 102 and the yoke. Such a sharp indentation may be undesirable with respect to reshaping the heart, and the heart may respond detrimentally to such severe indentation. The position of the actuator band and its predetermined shape may be adjusted to reduce the severity of the indentation or reshaping forces. Alternatively, in another embodiment of the invention, curvature limiting bands might be utilized in conjunction with the actuator band for controlling the shaping of the heart.

Figure 11B:
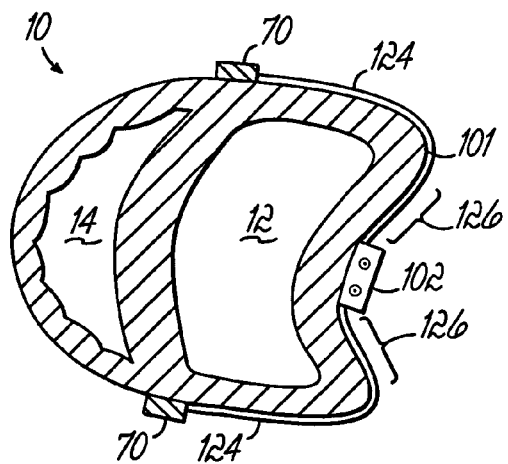

Specifically, referring to FIG. 11B, and FIGS. 3A-3B, curvature limiting bands 124 are shown illustrated with the actuator band 102. The curvature limiting bands are coupled to the actuator band, and more specifically are coupled between the actuator band and the yoke 70. The curvature limiting bands operate to limit the severity of the curvature or indentation in the heart wall 101 when the actuator band 102 is in an actuated state. That is, the bands 124 are operable for limiting the curvature that the actuator band imposes against the indented portion of the heart wall when it is actuated. The bands 124 include one or more rigid sections 126 which would engage the exterior heart wall adjacent to the actuator band to prevent certain portions of the wall from being overly distended upon indentation at the location of the actuator bands. Rather, the heart wall 101 will follow the curvature of the rigid curvature limiting bands and take a more gradual slope from the actuator band 102, as illustrated in FIG. 11B. The curvature limiting bands 124 cooperate with the actuator band for shaping the heart in the desired fashion and prevent too steep of an indentation or overly extended portions of the wall, based upon the indentation. In that way, the present invention achieves a more naturally shaped heart during actuation. Similar curvature limiting bands 124 might be utilized with the embodiment of the invention illustrated in FIGS. 5A and 5B.

Figure 12A:
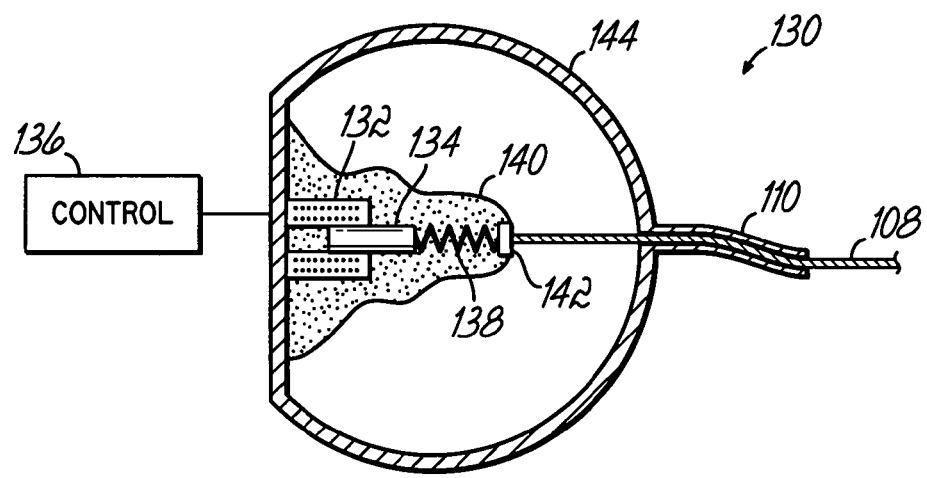
FIGS. 12A-12C illustrate cross-sectional views of a drive apparatus in accordance with one aspect of the present invention.
Figure 12B:
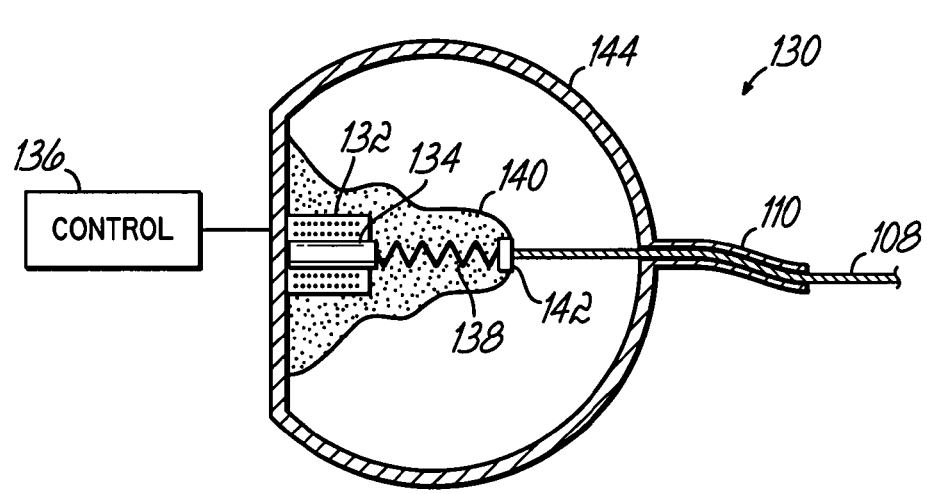

The heart at rest, as illustrated in FIG. 1, will have distended exterior heart walls which have a natural shape and curvature. Actuating a portion of the heart wall with the actuator band of the present invention will induce an indentation of the heart wall. The curvature limiting bands 124 limit the indentation or curvature induced or imposed against the heart wall by actuator band 102 to a certain increment from the natural curve of the heart wall exterior surface, along which the actuator band extends. That increment in curvature (the inverse of the radius of curvature usually expressed by the symbol 'κ' may be in the range of $\pm 1.0$ mm$^{-1}$. For example, in one embodiment, the actuator band should be configured to produce a curvature change from an initial value of $+0.02$ mm$^{-1}$ (i.e., convex with a radius of curvature of 50 mm) to a maximum of $+0.06$ mm$^{-1}$ (i.e., more convex with a radius of curvature of 16.33 mm) or to a minimum of $-0.02$ mm$^{-1}$ (i.e., concave with a radius of curvature of $-50$ mm). an indentation or shaping in the convex direction, as illustrated in FIGS. 12A and 12B, which is limited to between 2.5-3.0 times the curvature value of the natural heart 10 during the diastolic portion of the cardiac cycle. The curvature limiting bands are operable to control the curvature of the heart wall when the actuator band is in the actuated state. However, the curvature limiting bands are also operable to relax, in the relaxed state, so that the natural heart may easily return to its natural distended shape.

Figure 12C:
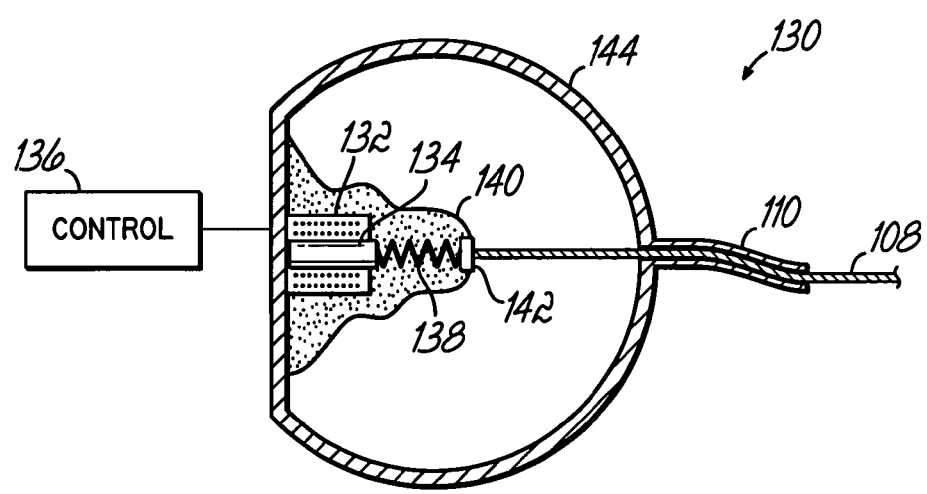

Turning now to the drive system for the present invention, various different drive systems may be suitable for the invention as disclosed specifically for drawing or tensioning the cable or cables 108. Referring to FIGS. 12A-12C, one embodiment of a drive apparatus is shown. Drive apparatus 130 comprises a solenoid, including a solenoid coil 132 and a solenoid plunger or armature 134. Cable 108 is coupled to the armature 134 for being drawn or tensioned upon activation of the solenoid coil 132. Appropriate controls and a power supply 136 are utilized for activating the solenoid coil 132 and drawing or tensioning cord 108. Drive apparatus 130 also includes an energy storing device coupled between the driver, such as the solenoid, and the cords 108. In the embodiment shown in the Figures, the energy storing device is a resilient coil spring structure 138. To move the actuator band 102 to an actuated state, control 136 energizes the coil 132 which draws armature 134. The cord 108 is drawn, in turn, and the actuator band assumes the desired shape, as discussed above. Referring to FIG. 12B, when the armature 134 moves, coil spring structure 138 is stretched, such that the cord 108 is not immediately drawn or tensioned. Rather, the coil spring 138 stretches, storing potential energy. Subsequently, coil spring structure 138 returns to its normal shape and draws or tensions cord 108 as illustrated in FIG. 12C. In that way, the immediate indentation forces on the heart are somewhat dampened by the resilient coil spring structure 138 to reduce the harshness of the heart deformation. Ultimately, the rate of motion of the deformation of the heart is determined by a balance between the force which is delivered by the actuator band against the exterior heart wall surface and the impedance of blood exiting from the cardiac chamber which is being shaped.

In the embodiment illustrated in FIGS. 12A-12C, the solenoid and energy storing device 138 are coupled inside of a resilient fluid-filled chamber or envelope 140. The chamber or envelope 140 is formed of a suitable elastomer and is filled with a bio-compatible fluid or oil, such as methyl silicone oil. The oil ensures smooth movement of the solenoid plunger or armature 134. As may be seen in FIG. 12B, a grommet 142 may be utilized to couple the cord 108 to spring 138. The grommet is formed with the envelope 140, such that the grommet moves to change the shape of the envelope upon tensioning and relaxation of the cord 108. For example, as illustrated in FIG. 12C, when the armature is drawn, and the spring returns to its rest position, the envelope 140 is compressed in length.

The solenoid, spring, and envelope are contained within a frame 144 which may be positioned subcutaneously within a patient, remotely from the actuator system. Coupled to or formed integrally with frame 144 is a portion of the sheath 110 through which cord 108 moves. The sheath and cord 108 provide mechanical coupling to the actuator system at the heart 10. Frame 144 contains a fixed geometric relationship between the end of the sheath 110 proximate the drive system, and the windings of the solenoid coil 132. One particular advantage of this arrangement is that a wear-prone part of the drive assembly, such as the envelope 140, may be placed in an easily accessible location, away from heart 10, where it may be replaced at particular maintenance periods, which may have several months or a few years therebetween. Generally, the drive system 130 will utilize a power supply (not shown), which may be part of the control 136. A further purpose of this design is that the tissue (soft connective tissue, such as body wall fat) in which it is placed will undergo relatively small cyclic strains. For example, the distance between grommet 142 and frame 144 increases by no more than 25% cyclically between the state shown in FIG. 12A and the state shown in FIG. 12C.

To position the invention into the body and around an existing natural heart 10, open heart thoracic surgery is required. Clinically, sufficient anesthesia is administered to the patient and the thoracic cavity is opened using standard thoracic procedures.

Once the thoracic cavity is opened, circulation of blood to the natural heart 10 must be bypassed so the present invention can be inserted into the patient. Referring initially to FIG. 1, the superior vena cava 24, the inferior vena cava (not shown), and aorta 26 are cannulated. The circulatory system is connected to a cardiopulmonary bypass machine so that circulation and oxidation of the blood are maintained during the procedure. By way of example, the procedure discussed in detail will be for insertion of the present invention to assist in the activation and operation of the left ventricle 12.

Through an aortotomy and an interatrial groove left atriotomy, the first and second rings 56 an 58, respectively, are inserted and sutured in position. Preferably, the first ring 56 is positioned suprajacent the mitral annuli and the second ring 58 is positioned subjacent the aortic annuli.

The interlocking struts of the septal frame 53 are inserted into the right ventricle 14 through an apical ventriculotomy, a right atriotomy with partial temporary detachment of the septal tricuspid leaflet of the tricuspid valve, and an outflow tract ventriculotomy, respectively. Suture 55 strands are then passed back and forth against the interventricular septum, threading through loops to provide a septal splint 54. In placement of both the various struts of frame 53 and the strands 55 that form splint 54, care is taken to maneuver behind chordae and behind or through major trabeculae and bases of papillary muscles. The suture strands 55 are tied to form the net-like configuration of the septal splint 54 that lies snugly against the septum, but allows it to maintain normal rightward convexity. Separate connector elements 59, preferably pins, are placed to join the first ring 56 and the second ring 58, the second ring 58 and the septal splint 54, and the septal splint 54 and the first ring 56.

Next, the free wall of the left ventricle is accessed either by retraction of the pericardium or opening of the left pleural cavity. Yoke 70 is positioned at the margins of the left ventricular free wall of the natural heart 10. Cords 86 may be assembled as 12 inch strands of suture with a polymer bead fused to one end and a blunt needle on the other. In that event, each suture is placed through a hole in the yoke 70, through the cardiac tissue, preferably the ventricular wall, and through the internal stint 52 (i.e. first ring 56 or septal splint) and anchored after length adjustment, with the excess portion of the sutures cut and removed. Cords 86 are tightened to render the intrinsically flexible stint 52 relatively taut and control bulging, preferably in a rightwardly direction.

Cardiotomies are closed, and the actuator band 102 is attached to the yoke 70. The cords 108 are attached to the drive apparatus and all indicated monitoring lines are positioned, as is usually done at the completion of cardiac operations. Termination of a cardiopulmonary bypass is attempted and, if successful, the thoracotomy is closed.

An alternative method for positioning the present invention includes removing the natural heart 10 from the patient, as discussed above, and auto-transplanting the natural heart 10 back into the patient using standard cardiectomy and cardiac transplant techniques known in the industry.

While the present invention has been illustrated by the description of the embodiments thereof, and while the embodiments have been described in considerable detail, it is not the intention of the applicant to restrict or in any way limit the scope of the appended claims to such detail. Additional advantages and modifications will readily appear to those skilled in the art. Therefore, the invention in its broader aspects is not limited to the specific details representative apparatus and method, and illustrative examples shown and described. Accordingly, departures may be made from such details without departure from the spirit or scope of applicant's general inventive concept.

What is claimed is:

1. An actuation system for assisting the operation of the natural heart, the actuation system comprising:
    a framework for interfacing with a natural heart;
    an actuator system coupled to the framework and configured to engage an exterior surface of the heart, the actuator system comprising:
    an actuator band extending along a portion of a heart wall exterior surface, the actuator band selectively movable between an actuated state and a relaxed state and operable, when in the actuated state, to assume a predetermined shape and thereby indent a portion of the heart wall to effect a reduction in the volume of the heart; and
    a plurality of curvature limiting devices including a plurality of curvature limiting bands coupled between the actuator band and the framework and operable for limiting the curvature that the actuator band imposes on the indented portion of the heart wall.

2. The actuation system of claim 1, further comprising a drive apparatus coupled to the actuator band and operable for selectively moving the actuator band between the relaxed and actuated states to achieve the desired assistance of the natural heart.

3. The actuation system of claim 1, wherein the actuator band is configured to extend along a portion of the left ventricle heart wall, and the band, in the actuated state is configured to indent the wall and effect a reduction of the volume of the left ventricle.

4. The actuation system of claim 1, wherein said actuator band includes a plurality of juxtaposed elements, the elements configured to be drawn together in the actuated state and to cooperate with each other, when drawn together, to assume the predetermined shape.

5. The actuation system of claim 4, wherein said elements are blocks coupled together by a cord, the cord operably coupled to be moved in the actuated state to draw the blocks together and form said predetermined shape.

6. The actuation system of claim 5, wherein said blocks have adjacent cooperating surfaces which are at least partially coextensive when the blocks are drawn together.

7. The actuation system of claim 5 further comprising a plurality of cords coupling the blocks together.

8. The actuation system of claim 5 wherein the cord extends through one of an aperture and a channel formed in the blocks to couple the blocks together.

9. The actuation system of claim 1, wherein at least one end of the actuator band is coupled to the framework.

10. The actuation system of claim 1 wherein said actuator band is coupled at both ends to said framework.

11. The actuation system of claim 1 wherein said curvature limiting device is operable for limiting the curvature of the actuator band to a certain percentage of the natural curve of the portion of a heart wall exterior surface along which the actuator band extends.

12. The actuation system of claim 1 further comprising a plurality of actuator bands for indenting a portion of the heart wall.

13. The actuation system of claim 1 wherein said actuator band comprises a plurality of articulated elements which move with respect to each other at joints.

14. The actuation system of claim 1 wherein the actuator band, in the relaxed state, is operable to generally assume the natural curve of the heart wall surface along which the actuator band extends.

15. An actuation system for assisting the operation of the natural heart, the actuation system comprising:
    a framework for interfacing with a natural heart;
    an actuator system coupled to the framework and configured to engage an exterior surface of the heart, the actuator system comprising:
    an actuator band extending along a portion of a heart wall exterior surface, the actuator band selectively movable between an actuated state and a relaxed state and operable, when in the actuated state, to assume a predetermined shape and thereby indent a portion of the heart wall to effect a reduction in the volume of the heart;
    a plurality of curvature limiting devices including a plurality of curvature limiting bands coupled between the actuator band and the framework and operable for limiting the curvature that the actuator band imposes on the indented portion of the heart wall; and
    a paving element positioned between the actuator band and the heart wall for providing smooth functioning of the band with the heart wall.

16. The actuation system of claim 15 wherein the paving element is flexible.

17. The actuation system of claim 15 wherein the paving element includes a mesh.

18. The actuation system of claim 15 wherein the paving element includes a fabric.

* * * * *